United States Patent [19]
Lemonnier

[11] Patent Number: 6,043,049
[45] Date of Patent: Mar. 28, 2000

[54] METHOD FOR DETECTING MICRO-ORGANISMS AND CARTRIDGE SUITABLE FOR IMPLEMENTING IT

[75] Inventor: Jean Lemonnier, Paris, France

[73] Assignee: Millipore S.A., Molsheim, France

[21] Appl. No.: 09/282,882

[22] Filed: Mar. 31, 1999

[30] Foreign Application Priority Data

Apr. 24, 1998 [FR] France .................................. 98 05165

[51] Int. Cl.[7] .................................................. C12Q 1/04
[52] U.S. Cl. ......................... 435/34; 435/4; 435/283.1; 435/287.1; 435/287.5; 422/50
[58] Field of Search ............................. 435/34, 4, 283.1, 435/287.1, 287.5; 422/50

[56] References Cited

U.S. PATENT DOCUMENTS

| | | | |
|---|---|---|---|
| 2,672,431 | 3/1954 | Goetz | 195/139 |
| 2,672,432 | 3/1954 | Goetz | 295/139 |
| 2,894,877 | 7/1959 | Sinden | 195/103.5 |
| 3,001,914 | 9/1961 | Andersen | 195/103.5 |
| 3,338,794 | 8/1967 | Bendt | 435/34 |
| 3,684,660 | 8/1972 | Kereluk et al. | 435/34 |
| 3,754,868 | 8/1973 | Witz et al. | 23/254 R |
| 3,886,047 | 5/1975 | Billups | 435/34 |
| 3,922,905 | 12/1975 | Roth | 435/34 |
| 4,326,028 | 4/1982 | Brown | 435/34 |
| 4,792,454 | 12/1988 | Lemonnier | 435/283.1 |
| 4,829,005 | 5/1989 | Friedman et al. | 435/296 |
| 5,556,591 | 9/1996 | Jallerat et al. | 264/516 |

FOREIGN PATENT DOCUMENTS

| | | |
|---|---|---|
| 0024048 | 2/1981 | European Pat. Off. . |
| 0 239 058 | 9/1987 | European Pat. Off. . |
| 0 450 850 | 10/1991 | European Pat. Off. . |
| 0 483 506 | 5/1992 | European Pat. Off. . |
| 2732692 | 10/1996 | France . |
| 196 08 009 | 10/1997 | Germany . |
| 1441576 | of 0000 | United Kingdom . |
| 2224118 | 4/1990 | United Kingdom . |
| WO94/03103 | 2/1994 | WIPO . |
| WO96/31594 | 10/1996 | WIPO . |

OTHER PUBLICATIONS

Search Report; from the "Institut National de la Propriete Industrielle,"French Application No. 9805165; dated Feb. 9, 1999; Examiner A. Coucke (2 pages).

Primary Examiner—Louise N. Leary
Attorney, Agent, or Firm—Jane Dana Hubbard; Timothy J. King

[57] ABSTRACT

The method uses a culture receptacle including a layer of growth medium (3), a first end surface of which gives onto a first chamber (27) and the second end surface of which gives onto a second chamber (28), and includes a step of causing a higher pressure in the first chamber (27) than in the second chamber (28), with a view to allowing the diffusion, in the layer of growth medium (3), of the water which the latter contains and optionally of a rehydrating solution (29) deposited on the first end surface of the layer of growth medium.

The cartridge has a body (2) with, between a grid (7) which the layer of growth medium (3) coats and an annular wall (8), a solid annulus (9) having towards the inside an extra thickness part forming a ridge (10).

17 Claims, 2 Drawing Sheets

METHOD FOR DETECTING MICRO-ORGANISMS AND CARTRIDGE SUITABLE FOR IMPLEMENTING IT

The invention relates in general terms to the detection of microorganisms such as bacteria, yeasts or moulds.

BACKGROUND OF THE INVENTION

It is known that, in order to effect this detection, receptacles are used containing a layer of growth medium for receiving micro-organisms coming from the environment which it is wished to monitor, the receptacle next being put to incubate at the required temperature and for the required time to enable the micro-organisms received to develop in the form of colonies visible to the naked eye, so that they can be counted and identified.

The invention aims to improve the conditions for the development, and therefore the counting and identification, of the organisms received on the layer of growth medium.

To this end it proposes a method for detecting microorganisms, characterized in that it includes the use of a culture receptacle having a layer of growth medium, a first end surface of which is adjacent a first chamber and the second end surface of which, opposite to the first, is adjacent a second chamber, and in that it includes a step of causing a higher pressure in said first chamber than in said second chamber.

The pressure difference then existing between the two end surfaces of the layer of the growth medium makes it possible, where its moisture level has become heterogeneous, to produce a diffusion of liquid inside this layer having the effect of rehomogenizing it, in particular at the surface receiving the micro-organisms.

The invention thus makes it possible to eliminate, or to very greatly reduce, the heterogeneity of the layer of growth medium, which is detrimental to the development of the micro-organisms and consequently to the counting and identification thereof.

According to preferred features, said receptacle is provided so that the first chamber is fluid tight, said step of causing a higher pressure including a step of closing this fluid tight chamber.

The step of causing a higher pressure is particularly easy and convenient to implement, the higher pressure resulting from a certain degree of compression of the volume of air trapped when the chamber is closed and/or the expansion of the air trapped in the chamber when the temperature rises due to placing in an incubator, where the fluid tight chamber has been closed in an environment at a temperature below that of the incubator.

According to other preferred features, the method according to the invention includes, prior to said step of causing a higher pressure, a step of striking said second end surface of the layer of growth medium with air jets.

Such a step of striking with air jets takes place in some air analysis apparatus in order to impact the micro-organisms present in the air on the layer of growth medium.

Causing a higher pressure is particularly advantageous after such a striking step as the air jets create craters in the layer of growth medium and dry the growth medium. By pressurizing of the surface opposite to the one which has been struck by the air jets, one causes a diffusion of liquid towards the dried surface, and therefore the rehomogenization of the layer of growth medium.

According to other preferred features, the method according to the invention includes a step of depositing a predetermined volume of rehydrating solution on said first end surface of the layer of growth medium prior to said step of causing a higher pressure. Such an addition of rehydrating solution, which will diffuse in the layer of growth medium by virtue of the pressurization, is particularly advantageous where the layer of growth medium has undergone a certain degree of drying, the existence of the higher pressure allowing excellent diffusion of the solution, appreciably greater than that able to be obtained simply by the effect of gravity.

The rehydrating solution can simply be water, or water with nutritive substances and/or specific dyes added. The diffusion procured by the higher pressure distributes these nutritive substances and/or dyes in the growth medium.

Thus, using a receptacle containing initially standard growth medium, it is possible to modify its properties in order to obtain a specific growth medium enabling certain predetermined micro-organisms to be counted and identified selectively.

According to other preferred features, the culture receptacle used has a grid coated with the layer of growth medium, which is oriented parallel to said grid. The presence of such a grid is particularly advantageous for providing a frame for the layer of growth medium (it is not possible to count on a holding of the layer of growth medium by means of an end surface, since each of these end surfaces must give onto a chamber).

The invention also relates, in a second aspect, to a cartridge for culturing micro-organisms, having a body with a grid and an annular wall oriented transversely to said grid and surrounding it, and having a layer of growth medium, preferably a gelled or self supporting medium such as agar; oriented parallel to said grid and coating it, characterized in that, in order to be suitable for the implementation of the method as disclosed above, said body has, between said annular wall and said grid, a solid annulus having towards the inside an extra thickness part forming a ridge.

This extra thickness ridge, because it is present towards the inside, remains coated by the layer of growth medium, even when the latter has undergone a certain shrinkage which has had the effect of separating its circumference from the annular wall of the body.

Given that the ridge remains coated and the annulus is solid, there is no possible passage between the circumference of the layer of growth medium and the body, so that the spaces situated inside the body respectively on each side of the layer of growth medium are separated in a fluid tight fashion, which makes possible the difference in pressure between the two end surfaces of layer of growth medium.

According to preferred features, for reasons of simplicity and convenience of manufacture of the cartridge and implementation of the method:

(a) the cartridge has a removable base adapted to be fitted onto said body in order to delimit an fluid tight chamber onto which a first end surface of said layer of growth medium is located; and preferably said base is fitted externally onto said annular wall of said body and has an internal surface coming into contact with the end surface of said annular wall situated on the same side as the base; and/or preferably said body and said base are made from molded plastic, said base being more flexible than said body; and/or (b) the cartridge has a removable cover adapted to be fitted onto said body in order to delimit a chamber in communication with the outside onto which a second end surface of said layer of growth medium gives; and preferably said cover has at least one hole allowing communication between the inside and outside of the cover when the latter is fitted onto said body; and/or preferably said cover is fitted externally onto said annular wall of said body and has an internal surface coming into contact with the end surface of said annular wall situated on the same side as the cover; and/or preferably said body and said cover are made from molded plastic, said cover being more flexible than said body.

According to other preferred features, in order to facilitate the counting of the colonies once the culturing has been effected, said grid has square meshes, and optionally is in a color contrasting with the layer of growth medium.

The disclosure of the invention will now be continued with the description of an example embodiment, given below for illustration and is not meant to be limiting in any manner.

DETAILED DESCRIPTION OF THE INVENTION

Figure 1:
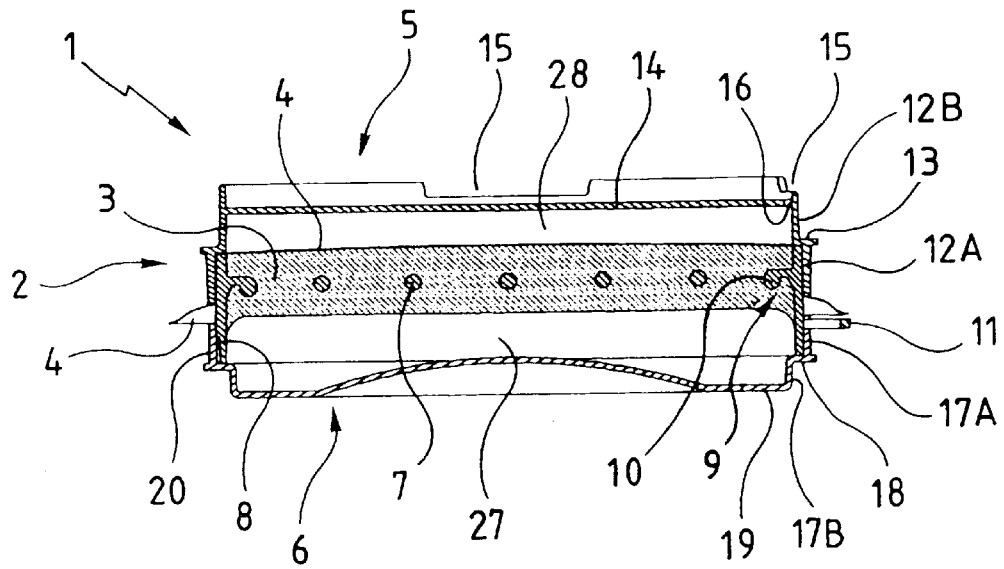
FIG. 1 is an elevation view in section through a cartridge according to the invention.

The illustrated cartridge 1 has a body 2, a layer of growth medium 3, a film 4, a cover 5 and a base 6. The body 2 is made from relatively rigid molded plastic material. It has a grid 7 and an annular wall 8 oriented transversely to the grid 7 and surrounding it. The grid 7 is formed by strands as can be seen notably in FIG. 1 with a circular cross section although others may be used, and it has square meshes, that is to say with four sides each having the same length, as can be seen in FIG. 2.

The periphery of the grid 7 is connected to the wall 8 by means of a solid annulus 9 having towards the inside, that is to say towards the grid 7, an extra thickness part forming a ridge 10, the extra thickness here being present solely on the side which faces the base 6 (there is no projection on the side which faces the film 4).

The annular wall 8 has a constant thickness and has the general shape of a relatively short tube with a circular cross section. Between its end surface on the same side as the film 4 and the annulus 9, the wall 8 extends over a predetermined length corresponding substantially to half the thickness provided for the layer 3 of growth medium, whilst it extends over a length approximately twice as great between the annulus 9 and its end surface situated on the same side as the base 6.

The growth medium is preferably a gelled medium or one that is self-supporting and capable of being formed into the present device. Any of the agar-based mediums is preferred.

Projecting lugs 11 extend transversely from the external surface of the wall 8, the distance between the lugs 11 and the end surface of the wall 8 situated on the same side as the film 4 being precisely identical for each of the lugs. Perforations are formed in each of the lugs 11. The latter are here four in number, and each has three perforations although other numbers may be used.

The film 4 is made from flexible fluid tight plastic material. It is initially in the shape of a square with rounded corners, with sides appreciably longer than the diameter of the external surface of the wall 8. Once the cover has been installed, the corners of the film form protuberances that facilitate its gripping.

The cover 5 is made from semi-rigid molded plastic material, which is therefore more flexible than the material of the body 8. It has the general shape of a bowl, the lateral wall of which consists of two tubular parts with a circular cross section 12A and 12B and an annular part 13 oriented transversely to the parts 12A and 12B between which it is disposed.

The part 12A has an internal diameter which is very slightly greater than that of the external diameter of the wall 8, so that the part 12A can be fitted with a certain amount of gripping around the wall 8 with the film 4 interposed between this wall and the part 12A.

The part 12B has an internal diameter which is smaller than that of the part 12A, the internal surfaces of the parts 12A and 12B being connected by an annular surface provided by the part 13, the dimensions of this annular surface corresponding to those of the end surface of the wall 8 situated on the same side as the film 4, so that the latter can be applied closely to this end surface of the wall 8 when the cover 5 is pushed onto the body 8 until it comes into abutment.

The cover 5 is closed by a flange 14 formed by a flat wall connected by its periphery to the internal surface of the part 12B of the lateral wall, the flange 14 being oriented transversely to this part. The flange 14 is disposed at a relatively great distance from the end of the part 12B which is connected to the part 13. The part 12B has a portion situated between the flange 14 and its free end in which indentations 15 are formed. Four small holes 16 are formed in the flange 14 at its junction with the part 12B of the lateral wall, respectively level with the center of each of the indentations 15.

The base 6 is made from semi-rigid molded plastic material, just as the cover 5. Like it, it has the general shape of a bowl, the lateral wall of which is formed by two tubular parts 17A and 17B with a circular cross section and by an annular part 18 oriented transversely to the parts 17A and 17B between which it is disposed. The internal diameter of the part 17A corresponds to the external diameter of the wall 8 that the part 17A can be fitted onto the wall 8 with its internal surface in close contact with the external surface of the wall 8.

Figure 2:
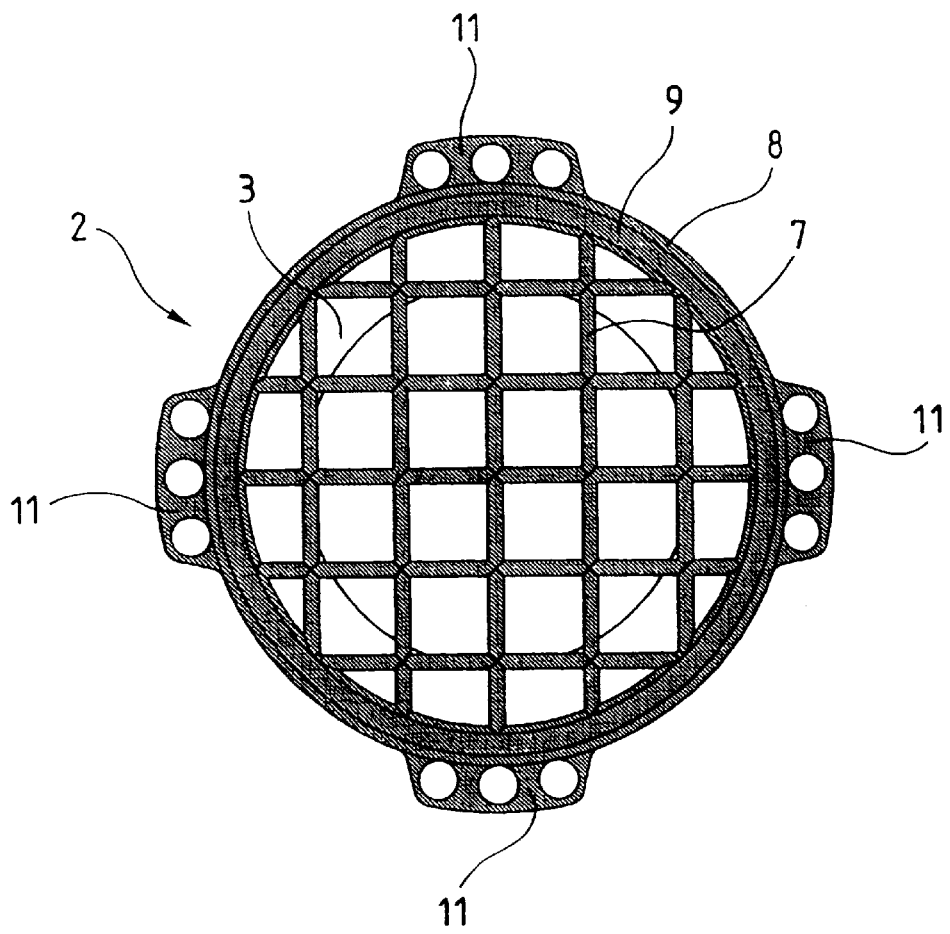
FIG. 2 is a plan view of this cartridge in which the cover, the film and the layer of growth medium are not depicted.
Figure 5:
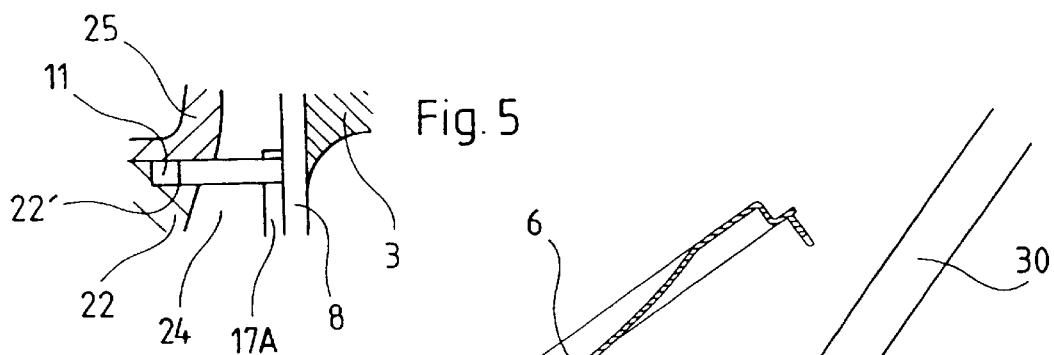
FIG. 5 is a partial elevation view in section showing the cooperation of the lugs on the cartridge with this apparatus.

Indentations are formed at the end of the part 17A to enable the lugs 11 to be housed, as can be seen on the right in FIG. 1 and in FIG. 5.

The internal diameter of the part 17B is smaller than that of the part 17A, the internal surfaces of the parts 17A and 17B being connected by an annular surface oriented transversely to the internal surfaces of the parts 17A and 17B, this annular surface being provided by the part 18 and being designed to come into close contact with the end surface of the wall 8 on the same side as the base 6.

A flange 19 with a convex surface on the inside closes off the base 6, this flange being connected transversely to the end of the part 17B opposite to the one by which the latter is connected to the part 18.

When the base 6 is pushed until it comes into abutment on the body 8, that is to say with the lugs 11 housed in the indentations in the part 17A and the part 18 in abutment on the wall 8, there is fluid tightness between the body 2 and base 6.

It is also possible to position the cover 6 that it is no longer the indentations situated at the end of the part 17A which are facing the lugs 11, but the projections situated between the indentations, so that the base 6 is pushed onto the body 2 only as far as a position in which the free end of the projections on the part 17A come to bear on the lugs 11.

In this position, the small slots 20 formed externally in the wall 8 over a certain length as from its free end on the same side as the base 6 are no longer completely masked by the base 6 (the part 17A surrounds the wall 8 over a lesser distance than the length of the slots 20) so that there is communication with the outside by means of the slots 20.

An explanation will now be given how the cartridge 1 is manufactured and how it is sterilized.

First of all the film 4 is disposed on the corresponding end surface of the wall 8, and then the cover is fitted onto the body 2, which provides a tensioning of the film 4 because the internal surface of the part 12A of the lateral wall of the cover 5 slides over the film beyond the end surface of the wall 8 and therefore tends to drive the film along the external surface of this wall, the film being held, at the end of the fitting-on movement, between the external surface of the wall 8 and the internal surface of the part 12A and between the end surface of the wall 8 and the annular surface which is situated between the internal surfaces of the parts 12A and 12B. By virtue of the small holes 16, any difference in pressure between the two sides of the film 4 liable to deform it is avoided.

The film 4, which is thus tensioned and wedged by the cover 5, is in sealed contact with the wall 8.

The base 6 is then fitted into the position where it is the projections on the parts 17A which come to bear on the lugs 11, that is to say in the position in which the small slots 20 are not completely masked.

The cartridge is then placed in a chamber containing a sterilization gas such as ETO, this gas entering the cartridge through the holes 16 in the cover 5 and through the slots 20 in the wall 8.

Figure 3:
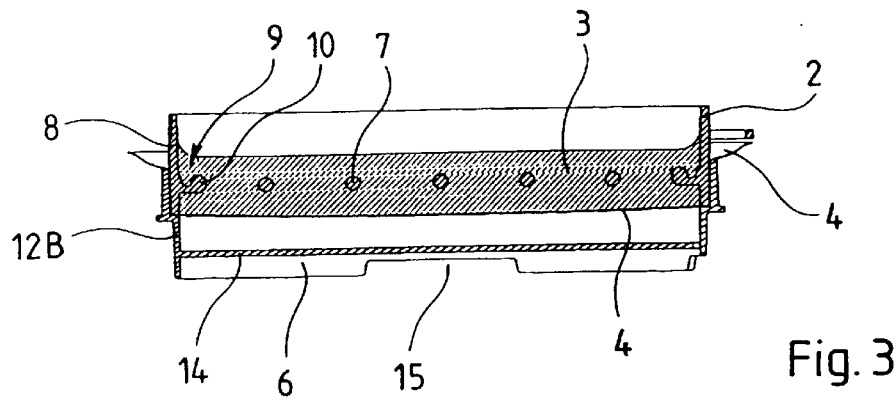
FIG. 3 is an elevation view in section of the cartridge, in the upturned position and without the base.

Once the sterilization has been effected, working under aseptic conditions, the base 6 is removed, the assembly consisting of the body 2, film 4 and cover 5 is turned over and placed on the kind of tripod formed by the portion of the part 12B situated beyond the flange 14, and then growth medium, previously heated to make it liquid, is poured into the bowl formed by the body 8 and film 4 until it covers the grid 7, as shown in FIG. 3, and after cooling of the growth medium the base 6 is positioned so that the indentations on the part 17A are opposite the lugs 11, and the base 6 is pushed in completely.

The cartridge 1 is then in the configuration shown in FIG. 1. It will be noted that, in this configuration, the layer of growth medium 3 is kept completely sterile since it is kept away from any contact with the outside.

Because the ridge 10 on the annulus 9 has no projection on the side facing the film 4, this ridge does not interfere with the filling of the space situated between the film 4 and annulus 9 when the growth medium is poured.

The ridge 10, because it projects on the inner side of the annulus 9, remains completely coated by the layer of growth medium 3, even if the latter undergoes shrinkage having the effect of separating its periphery from the annular wall 8 of the body 2. Thus such a shrinkage does not cause any break in the fluid tightness inside the body 2 between the spaces situated on each side of the layer of the growth medium 3.

By virtue of this fluid tightness and the one existing between the body 2 and cover 6, the space which faces the end surface of the layer of growth medium 3 opposite to the one delimited by the film 4 forms a fluid tight chamber in which a certain overpressure can exist, as explained below.

Figure 4:
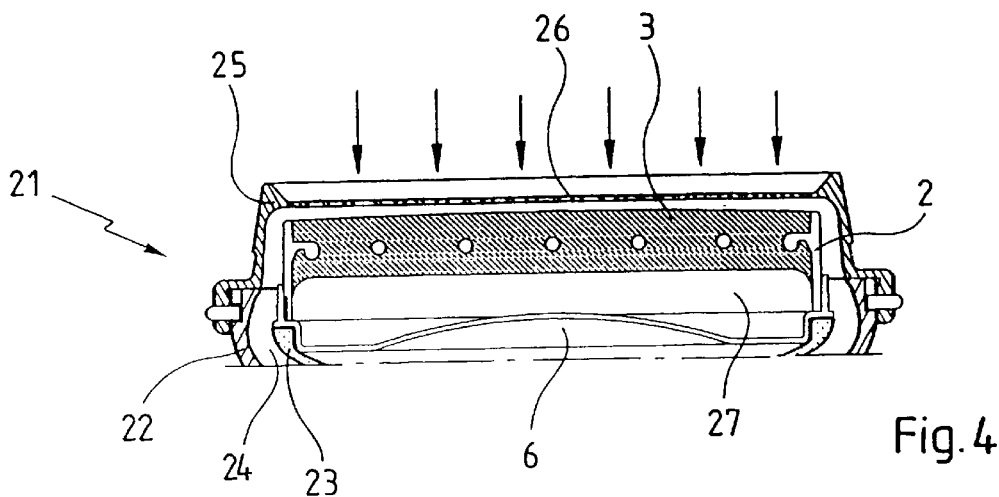
FIG. 4 is an elevation view in section showing this cartridge, the cover and film of which have been removed, fitted in an apparatus for taking an air sample and for the impact on the layer of growth medium of the microorganisms present in this sample.

The cartridge 1 has been designed to effect an analysis of a sample of air using the machine 21 shown partially in FIG. 4, which serves to deposit the micro-organisms present in the sample of air on the surface of the layer of growth medium 3 delimited by the film 4.

The machine 21 has an aerodynamic sleeve 22 on which a deflector 23 is mounted, so that there exists around the deflector 23 a conduit 24 for the flow of air towards a suction turbine, not shown.

A removable sieve 25 is mounted on the end of the sleeve 22 which is provided with notches 22' (FIG. 5) in order to receive the end of the lugs of a cartridge 1 whose cover 5 and film 4 have been removed, the sieve 25 having a central wall 26 situated exactly opposite the surface of the layer of growth medium 3 which was delimited by the film 4, a multitude of fine perforations being formed in the wall 26.

When the turbine (not shown) of the apparatus 21 operates, the external air is sucked in, as shown by the arrow, through the perforations in the wall 26 and then flows towards the turbine in the conduit 24, the end of the deflector 23 being closed off by the base 6.

The flow of air between the layer of growth medium 3 and the wall 26 takes place in the form of a multitude of fine jets each corresponding to a perforation. These air jets strike the layer of growth medium 3, the micro-organisms present in the air which thus strikes the layer of growth medium being fixed on the latter by impaction.

It will be observed that the separation between the layer of growth medium 3 and the perforated wall 26 of the sieve 25 has geometric characteristics which are repeated from one cartridge to another, the use of the film 4 for forming the surface of the layer 3 making it possible to fix precisely the positioning of this surface with respect to the body 2, the positioning of the latter with respect to the wall 26 being repeated from one cartridge to another by the fitting of the cartridge on the sleeve 22 by means of the lugs 11 so that, from one cartridge to another, the flow of air sucked in for each rotation of the turbine remains substantially the same, the speed of striking on the layer of growth medium 3 consequently remaining constant for the same speed of rotation of the turbine, just as the volume of air sucked in remains constant for the same number of rotations effected by the turbine.

The cooperation between the lugs 11 of the cartridge 1 and their receiving notches 22' situated at the end of the sleeve 22 provides both an axial positioning and a centering of the cartridge 1, only the end of the lugs 11, the free end of which is curved, being received in the notches.

The lugs 11 are then disposed across the conduit 24, but the perforations, here three in number, which are formed therein, allow passage of air to the turbine.

The cooperation between the cartridge 1 and the deflector 23 takes place with a certain amount of clearance, sufficient to close off the deflector, the cover 6 being fitted thereon internally, the external diameter of the part 17B being smaller than the internal diameter of the end of the deflector 23.

Once the required volume of air has been sucked in, the sieve 25 is removed from the machine 21, the cover is fitted in place again on the cartridge 1 and the latter is retrieved.

All that remains to be carried out, in a conventional fashion, is the culturing of the micro-organisms impacted on the layer 3, by placing the cartridge in an incubator heated to a predetermined temperature such as 32.5° C. (+/−2.5° C.) for the required time, for example two days, the cartridge 1, by virtue of the holes 16 in the cover 5, allowing the gaseous exchanges, notably aerobic, necessary to the development of the colonies.

The cartridge 1 is preferably turned over to effect the culturing, being placed on the kind of tripod formed by the portion of the part 12B of the lateral wall which extends beyond the flange 14, the indentations 15 allowing the circulation of air, the fact that the flange 14 is situated underneath the layer of growth medium 3 (and not on top) preventing, in a well-known fashion, the phenomena of condensation on the cover.

The space 27 delimited by the layer of growth medium 3, the wall 8 and the base 6 forming a fluid tight chamber, the air which is contained therein was put under slight overpressure when the base 6 was closed, and furthermore an additional overpressure will be created because this air expands when it takes the temperature of the incubator, which is in principle higher than the initial temperature of this volume of air.

The space 28 delimited by the layer of growth medium 3, the wall 8 and the cover 5 being in communication with the outside, notably through the holes 16, there exists, because of the overpressure in the chamber 27, a pressure difference between the two end surfaces of the layer of growth medium. This pressure difference assists the rehomogenization of the layer of growth medium 3, in particular at the surface that was impacted in the machine 21.

As a matter of fact, the air jets that struck this surface of the layer of growth medium 3 formed craters therein and caused a certain amount of drying which reduces the nutritive capabilities thereof.

This drying is relatively great: it is estimated for example that it is usual to lose 2 g of water for a sampled air volume of 1 m$^3$ out of a total of 34 g for the layer of growth medium 3.

Figure 6:
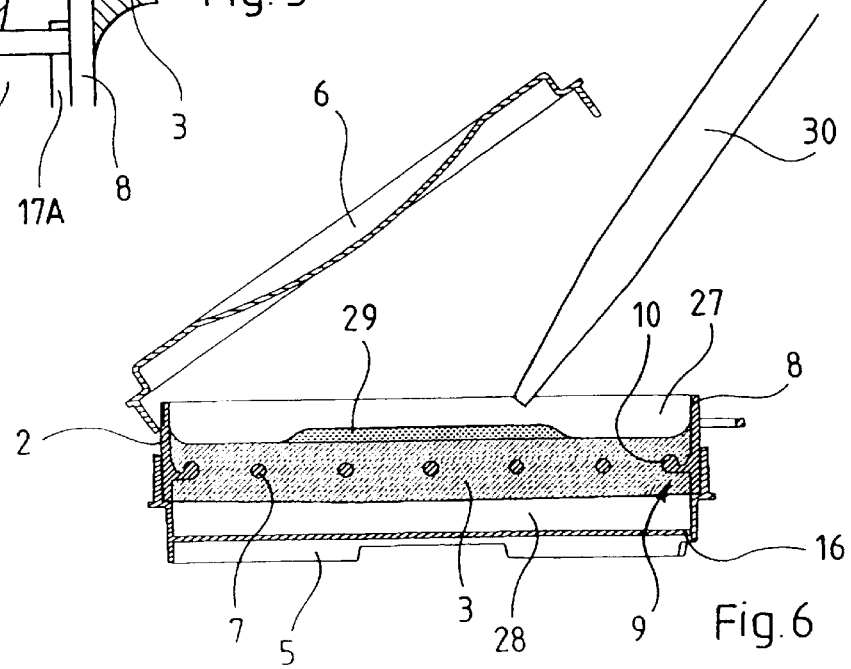
FIG. 6 is an elevation view in section showing this cartridge once again fitted with its cover, in the upturned position, with its base removed in order to deposit a predetermined volume of rehydrating solution on the layer of growth medium.

It is possible, rather than relying solely on the water remaining in the layer of growth medium 3 for rehydrating the impacted surface, to deposit a certain volume of rehydrating solution 29 on the layer 3, on the opposite side to the impacted surface, as shown in FIG. 6.

To carry out this deposition, the base 6 is removed and, using a pipette 30, the required volume of rehydrating solution 29, which corresponds for example to 80 or 90% of the dehydration established by weighing the cartridge 1, is deposited.

The rehydrating solution will reach as far as the opposite surface of the layer 3 by virtue of gravity, but also and particularly by virtue of the overpressure in the fluid tight chamber, which assists the diffusion of liquid, and notably of the solution 29, in the layer 3.

The rehydration of the impacted surface will cause the craters to disappear, which is beneficial to the development of the colonies and therefore facilitates their identification, the fact that the surface is smooth also assisting counting, and also the subculturing of the colonies requiring specific identification.

According to circumstances, the rehydrating solution contains only water or water mixed with nutritional substances and/or specific dyes permitting selective identification or growth of the micro-organisms impacted on the layer of growth medium.

It will be noted that the square shape of the meshes of the grid 7 advantageously gives the user an indication of the size of the surface on which the colonies have developed, each mesh delimiting for example a surface area of 1 cm$^2$. The growth medium being transparent, it is preferable for the grid 7 to be colored in order to be easily visible, the body 2 being for example molded from a black plastic. The cover 5 is transparent so that reading can be effected whilst the cartridge 1 remains closed.

It is of course understood that the cartridge according to the invention can be used for other types of analyses, for example in order to determine the contamination of a liquid, the surface of the layer of growth medium 3 which is delimited initially by the film 4 receiving a membrane through which the required volume of liquid to be analyzed is passed.

In a variant which is not shown, a culture receptacle without a film 4 is used, the latter being for example replaced by a cover serving solely for the manufacture and storage of the cartridge, this cover being replaced during use by a cover of the same type as the cover 5.

Numerous variants are possible according to circumstances, and it should be stated in this regard that the invention is not limited to the examples described and depicted.

What I claim:

1. Method for detecting micro-organisms comprising the steps of using a culture receptacle having a layer of growth medium, a first end surface of which gives onto a first chamber and the second end surface of which, opposite the first, gives onto a second chamber, and a step of causing a higher pressure in said first chamber than in said second chamber.

2. The method according to claim 1, wherein said receptacle is provided whereby said first chamber is fluid tight and said step of causing a higher pressure includes a step of closing said fluid tight chamber.

3. The method according to either one of claims 1 or 2, comprising a step of striking said second end surface of the layer of growth medium with air jets to deposit micro-organisms on the second end surface prior to said step of causing a higher pressure.

4. The method according to claim 1 further comprising the step of depositing a predetermined volume of rehydrating solution on said first end surface of the layer of growth medium prior to said step of causing a higher pressure.

5. The method according to claim 4 wherein water is used as a rehydrating solution.

6. The method according to claim 4 wherein the rehydrating solution is formed of water with one or more additional substances selected from the group consisting of nutritive substances and dyes.

7. The method according to claim 1 wherein said receptacle has a grid coated with the layer of growth medium, which is oriented parallel to said grid.

8. A cartridge for culturing micro-organisms comprising a body with a grid and an annular wall oriented transverse to said grid and surrounding said grid which is coated by a layer of growth medium oriented parallel to said grid and said body has between said annular wall and said grid, a solid annulus having towards the inside an extra thickness part forming a ridge.

9. The cartridge according to claim 8 wherein the cartridge has a removable base adapted to fit onto said body in order to delimit a fluid tight chamber onto which a first end surface of said layer of growth medium resides.

10. The cartridge according to claim 9 wherein said base is fitted externally onto said annular wall of said body and has an internal surface coming into contact with the end surface of said annular wall situated on the same side as the base.

11. The cartridge of claim 9 wherein said body and said base are made from molded plastic, said base being more flexible than said body.

12. The cartridge according to any one of claims 8 to 11 wherein it has a removable cover adapted to fit onto said body in order to delimit a chamber in communication with the outside onto which a second end surface of said layer of growth medium resides.

13. The cartridge according to claim 12 wherein said cover has at least one hole allowing communication between the inside and outside of the cover when the latter is fitted onto said body.

14. The cartridge according to either one of claims 12 or 13, wherein said cover is fitted externally onto said annular wall of said body and has an internal surface coming into contact with the end surface of said annular wall situated on the same side as the cover.

15. The cartridge according to any one of claims 12 to 14 wherein said body and said cover are made from molded plastic, said cover being more flexible than said body.

16. The cartridge according to claim 8 wherein said grid has square meshes.

17. The cartridge according to claim 8 wherein said grid is in a color contrasting with said layer of growth medium.

* * * * *